United States Patent
Allen et al.

(10) Patent No.: US 9,988,322 B2
(45) Date of Patent: Jun. 5, 2018

(54) PROCESS FOR FLUORINATING COMPOUNDS

(71) Applicants: Dow AgroSciences LLC, Indianapolis, IN (US); The Regents of the University of Michigan, Ann Arbor, MI (US)

(72) Inventors: Laura Allen, Ypsilanti, MI (US); Melanie Sanford, Ann Arbor, MI (US); Douglas Bland, Midland, MI (US)

(73) Assignees: Dow AgroSciences LLC, Indianapolis, IN (US); Regents of the University of Michigan, Ann Arbor, MI (US)

( * ) Notice: Subject to any disclaimer, the term of this patent is extended or adjusted under 35 U.S.C. 154(b) by 0 days. days.

(21) Appl. No.: 14/539,613

(22) Filed: Nov. 12, 2014

(65) Prior Publication Data

US 2015/0133672 A1    May 14, 2015

Related U.S. Application Data

(60) Provisional application No. 61/902,979, filed on Nov. 12, 2013, provisional application No. 61/985,224, filed on Apr. 28, 2014.

(51) Int. Cl.
  *C07D 213/79* (2006.01)
  *C07B 39/00* (2006.01)
  *C07D 213/803* (2006.01)

(52) U.S. Cl.
  CPC ............ *C07B 39/00* (2013.01); *C07D 213/79* (2013.01); *C07D 213/803* (2013.01)

(58) Field of Classification Search
  None
  See application file for complete search history.

(56) References Cited

U.S. PATENT DOCUMENTS

| | | |
|---|---|---|
| 7,592,486 B2 | 9/2009 | DiMagno et al. |
| 7,939,697 B2 | 5/2011 | Hagiya |
| 2004/0144947 A1 | 7/2004 | Garayt et al. |
| 2006/0009643 A1 | 1/2006 | Pleschke et al. |
| 2012/0190857 A1 | 7/2012 | Arndt et al. |
| 2012/0190858 A1 | 7/2012 | Zhu et al. |
| 2012/0190859 A1 | 7/2012 | Zhu et al. |
| 2012/0190860 A1 | 7/2012 | Whiteker et al. |
| 2014/0031556 A1 | 1/2014 | Renga et al. |
| 2014/0031558 A1 | 1/2014 | Renga et al. |
| 2014/0171650 A1 | 6/2014 | Giampietro et al. |
| 2014/0171653 A1 | 6/2014 | Renga et al. |
| 2014/0171654 A1 | 6/2014 | Johnson et al. |
| 2014/0206881 A1 | 7/2014 | Zhu et al. |
| 2014/0296533 A1 | 10/2014 | Renga et al. |
| 2015/0133672 A1 | 5/2015 | Allen et al. |
| 2015/0141654 A1 | 5/2015 | Allen et al. |

FOREIGN PATENT DOCUMENTS

| | | |
|---|---|---|
| EP | 0146924 A2 | 12/1984 |
| EP | 1698606 A1 | 9/2006 |
| WO | 2002092608 A2 | 11/2002 |
| WO | 2003076366 A2 | 9/2003 |
| WO | 2003106379 A1 | 12/2003 |
| WO | 2004048350 A2 | 6/2004 |
| WO | 2006055748 A2 | 5/2006 |
| WO | 2012163905 A1 | 12/2012 |

OTHER PUBLICATIONS

Kuduk, SD. et al. Tetrabutylammonium Salt Induced Denitration of Nitropyridines: Synthesis of Fluoro-, Hydroxy-, and Methoxypyridines. Organic Letters. 2005, vol. 7, p. 578.*
Sun, H. et al. Room-Temperature Nucleophilic Aromatic Fluorination: Experimental and Theoretical Studies. Angew. Chemie. 2006, vol. 45, p. 2721.*
Sun, H. et al. Anhydrous Tetrabutylammonium Fluoride. JACS Communications. 2005, vol. 127, p. 2050.*
International Search Report and Written Opinion for PCT/US2014/065212 dated Mar. 31, 2015.
Restriction Requirement U.S. Appl. No. 14/539,696, dated Aug. 11, 2015.
Notice of Allowance U.S. Appl. No. 14/539,700, dated Aug. 19, 2015.
Anbarasan et al., Efficeient Synthesis of Aryl Fluorides, Angew. Chem., Int. Ed., 49:2219-2222, 2010.
Balz et al., On aromatic fluorine compounds, I.: A new process for their preparation Ber. Deutsch. Chem. Ges., 60:1186, 1927.
Barnette et al., N-Fluoro-N-alkylsulfonamides: Useful Reagents for the Fluorination of Carbanions, J. Am. Chem. Soc., 106:452-454, 1984.
Cox et al., "Anhydrous" Tetrabutylammonium Fluoride: A Mild but Highly Efficient Source of Nucleophilic Fluoride Ion, J. Org. Chem., 49:3216-3219, 1984.
Differding et al., Nucleophilic Substitution Versus Electron Transfer: 2.SH1 at Fluorine and Electron Transfer are and Competing Different Pathways in Electrophilic Fluorinations, Tetrahedron Lett., 32:3819-3822, 1991.
Heinz et al. A simple synthesis of tetraalkylammonium salts with functional anions. Justis Liebig Annalen der Chemie,6 12:1937, 1978.
Higgins et al., PKas of the conjugate acids of N-heterocyclic carbenes in water, Chem. Commun., 47:1559-1561, 2011.
Kim et al., New Method of Fluorination Using Potassium Fluoride in Ionic Liquid: Significantly Enhanced Reactivity of Fluoride and Improved Selectivity, J. Am. Chem. Soc.. 124:10278-10279, 2002.

(Continued)

*Primary Examiner* — Heidi Reese
(74) *Attorney, Agent, or Firm* — Michael R. Asam; Meunier Carlin & Curfman, LLC

(57) ABSTRACT

Methods of preparing a fluorinated aryl or heteroaryl substrate by combining a quaternary ammonium cyanide and an aryl or heteroaryl substrate substituted with at least one chloro, bromo, sulfonyl, or nitro group to thereby provide a mixture, and combining the mixture with hexafluorobenzene to thereby provide the fluorinated substrate.

17 Claims, 1 Drawing Sheet

(56) References Cited

OTHER PUBLICATIONS

Liang et al., Introduction of Fluorine and Fluorine-Containing Functional Groups, Angewandte Chemie International Edition, 52:8214-8264, 2013.
Okamoto et al., Activity and behavior of imidazolium salts as a phase transfer catalyst for a liquid-liquid phase system, Tetrahedron Letters, 47:8055-8058, 2006.
Sharma et al., Instability of Anhydrous Tetra-N-alkylammonium Fluorides, J. Org. Chem., 48:2112-2114, 1983.
Sun et al., Anhydrous Tetrabutylammonium Fluoride, J. Am. Chem. Soc., 127:2050-2051, 2005.
Sun et al., Room-Temperature Nucleophilic Aromatic Fluorination: Experimental and Theoretical Studies, Angewandte Chemie International Edition, 45:2720-2725, 2006.
Walsh et al., Mutations in an Auxin Receptor Homolog AFB5 and in SGT1b Confer Resistance to Synthetic Picolinate Auxins and Not to 2,4-Dichlorophenoxyacetic Acid or Indole-3-Acetic Acid in Arabidopsis, Plant Physiology, 142:542-552, 2006.
Yamada et al., Convenient Electrophilic Fluorination of Functionalized Aryl and Heteroaryl Magnesium Reagents, Angew. Chem., Int. Ed., 49:2215-2218, 2010.
Zhong et al., Direct Formation of 2,3,5-Trichloropyridine and its Nucleophilic Displacement Reactions in Ionic Liquid. Synthetic Commun. 34(23):4301-4311, 2004.
Office Action from United States Patent Office for U.S. Appl. No. 14/529,700, dated Mar. 17, 2015.
International Search Report and Written Opinion for PCT/US2014/065272, dated Jan. 30, 2015.
International Search Report and Written Opinion for PCT/US2014/065199, dated Jan. 30, 2015.
Bobbio et al., Removal of Fluorine from and Introduction of Flourine into Polyhalopyridines: An Exercise in Nucleophilic Hetarenic Substitution. Eur. J. Chem. 11(6):1903-1910, 2005.
Allen et al., Mild Fluorination of Chloropyridines with in situ Generated Anhydrous Tetrabutylammonium Fluoride. J. Org. Chem. 17(12):5827-5833, 2014.
Allen et al., Developing Efficient Nucleophilic Fluorination Methods and Application to Substituted Picolinate Esters. Org. Proc. Res. Dev. 18(8):1045-1054, 2014.
Sagar et al., Synthetic studies towards the antiviral pyrazine derivative T-205. Proceedings of the 13th Electronic Conference on Synthetic Organic Chemistry Nov. 1-30, 2009, 13:1-3.
Maggini et al., A general procedure for the fluorodenitration of aromatic substrates. J. Org. Chem. 56(22):6406-6411, 1991.
Sasson et al., Tetramethylammonium chloride as a selective and robust phase transfer catalyst in solid-liquid halex reaction: the role of water. Chem. Commun. 197-298, 1996.
Notice of Allowance for U.S. Appl. No. 14/539,696 dated Jul. 12, 2016.
Notice of Allowance for U.S. Appl. No. 15/228,188 dated Sep. 20, 2017.
Office Action for U.S. Appl. No. 15/228,188 dated Apr. 4, 2017.
Boechat et al., Fluorodenitration using tetramethylammonium fluoride, J. Chem Soc. Chem. Commun. 11:921-922, 1993.
Office Action for U.S. Appl. No. 14/539,696 dated Feb. 19, 2016.

\* cited by examiner

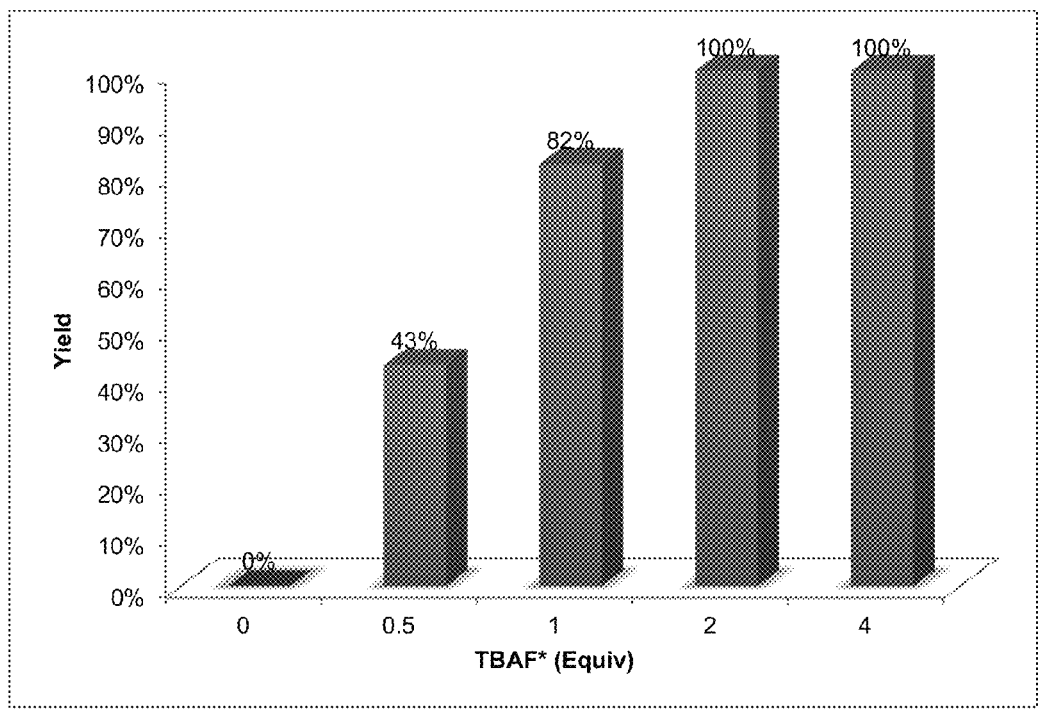

PROCESS FOR FLUORINATING COMPOUNDS

CROSS REFERENCE TO RELATED APPLICATIONS

This application claims the benefit of U.S. Provisional Patent Application Ser. No. 61/902,979 filed Nov. 12, 2013, and U.S. Provisional Patent Application Ser. No. 61/985,224 filed Apr. 28, 2014, the entire disclosures of which are expressly incorporated herein by reference.

FIELD

This application relates generally to methods of fluorinating aryl or heteroaryl compounds and to fluorinated compounds.

BACKGROUND

Fluorinated organic molecules are increasingly used in life science industries. The presence of a fluorine substituent can have positive effects on the biological properties of compounds. Thus, synthetic techniques for fluorinating compounds are a significant area of interest.

The selective fluorination of aryl and heteroaryl substrates is a challenging synthetic problem. As an example, mono- and di-chloro substituted picolinate esters are difficult to fluorinate and require more expensive metal fluorides (e.g., cesium fluoride (CsF)) to generate acceptable yields. Under Halex (halogen exchange) conditions, which use potassium fluoride, the chemical yields are often quite low (<20%). Also, Halex conditions usually require a phase transfer catalyst, a high boiling solvent, and high temperatures. Such conditions can preclude the use of Halex conditions in many systems.

Tetrabutylammonium fluoride (TBAF) has been used as a highly nucleophilic fluoride-ion source to fluorinate a variety of substrates. This reagent is prepared by treating tetrabutylammonium cyanide with hexafluorobenzene in a solvent and under anhydrous conditions. The resultant TBAF (i.e., TBAF$_{anh}$ or TBAF*) can then be used to fluorinate certain substrates. See DiMagno et al. *J. Am. Chem. Soc.* 2005, 127, 2050-2051; DiMagno et al. *Angew. Chem. Int. Ed.* 2006, 45, 2720-2725.

While TBAF* has been successful in certain systems, it has limitations, such as poor selectivity and reactivity for difficult substrates like chloropyridines, especially those of the 6-arylpicolinate family. Other limitations include the necessity for pre-formation of TBAF* for every batch of reactions and fluorinations demonstrated in only DMSO. What are needed are new methods for fluorinating compounds and the methods and compounds disclosed herein address these and other needs.

SUMMARY

The subject matter disclosed herein relates to methods of making compositions and the compositions themselves. In particular, the subject matter disclosed herein relates generally to methods of fluorinating aryl or heteroaryl compounds and to fluorinated compounds. In certain specific aspects, disclosed herein are methods of preparing a fluorinated aryl or heteroaryl substrate that comprise combining a quaternary ammonium cyanide and an aryl or heteroaryl substrate substituted with at least one chloro, bromo, sulfonyl, or nitro group to thereby provide a mixture. The mixture is combined with hexafluorobenzene to thereby provide the fluorinated substrate. In the disclosed methods, the quaternary ammonium cyanide and the aryl or heteroaryl substrate can be combined in the presence of a solvent, or alternatively or additionally, the hexafluorobenzene and the mixture can be combined in the presence of a solvent. The solvent can even be added to the mixture before combining the mixture with hexafluorobenzene. One advantage of the disclosed methods is that one or more of the steps can be conducted at or about room temperature and the selectivity of the reaction is relatively high.

The disclosed methods are particularly well suited for fluorinating heteroaryl substrates having Formula IA or IB:

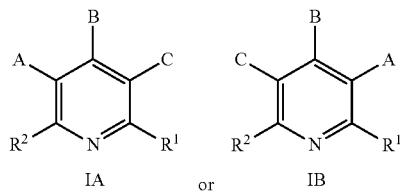

wherein A is Cl, Br, SO$_2$R$^3$, or NO$_2$; B is H, Cl, Br, SO$_2$R$^3$, or NO$_2$; C is H, Cl, Br, SO$_2$R$^3$, or NO$_2$; R$^1$ is H, CN, or CO$_2$R$^3$, wherein each R$^3$ is, independent of any other, optionally substituted C$_1$-C$_{12}$ alkyl, C$_2$-C$_{12}$ alkenyl, C$_2$-C$_{12}$ alkynyl, heterocycloalkyl, heteroaryl, cycloalkyl, or aryl; and R$^2$ is H, substituted or unsubstituted aryl, substituted or unsubstituted heteroaryl. Such substrates are particularly difficult to fluorinate. One of the resulting products of the disclosed methods upon substrates having Formula IA or IB is a compound having Formula IIA or IIB

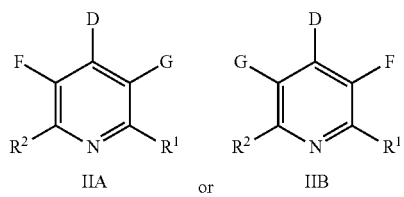

wherein D is B, as is defined above, or F, and G is B, as is defined above, or F. The disclosed products represented by Formula IIA or IIB are often obtained in greater yields than the difluorinated or para-fluorinated products, indicating the fluorinating process disclosed herein is relatively selective.

In other aspects, the subject matter disclosed herein relates to methods of preparing a fluorinated heteroaryl substrate that comprises mixing a quaternary ammonium cyanide, hexafluorobenzene, a solvent, and a heteroaryl substrate having Formula IA or IB wherein A is Cl, Br, SO$_2$R$^3$, or NO$_2$; B is H, Cl, Br, SO$_2$R$^3$, or NO$_2$; C is H, Cl, Br, SO$_2$R$^3$, or NO$_2$; R$^1$ is H, CN, or CO$_2$R$^3$, wherein each R$^3$ is, independent of any other, optionally substituted C$_1$-C$_{12}$ alkyl, C$_2$-C$_{12}$ alkenyl, C$_2$-C$_{12}$ alkynyl, heterocycloalkyl, heteroaryl, cycloalkyl, or aryl; and R$^2$ is H, substituted or unsubstituted aryl, substituted or unsubstituted heteroaryl.

In still other aspects, the subject matter disclosed herein relates to products prepared by the methods disclosed herein. In still other aspects, the subject matter disclosed herein relates to fluorinated compounds, such as those prepared by the disclosed methods.

Additional advantages of the disclosed subject matter will be set forth in part in the description that follows and the FIGURE, and in part will be obvious from the description, or can be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURE

The accompanying FIGURE, which is incorporated in and constitutes a part of this specification, illustrates several aspects described below.

FIG. 1 is a graph showing fluorination of model substrate DS-2 with pre-formed TBAF*.

DETAILED DESCRIPTION

The materials, compounds, compositions, articles, and methods described herein may be understood more readily by reference to the following detailed description of specific aspects of the disclosed subject matter and the Examples and FIGURE included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, reference to "an agent" includes mixture of two or more such agents, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect.

Chemical Definitions

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"$Z^1$," "$Z^2$," "$Z^3$," and "$Z^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkoxy" as used herein is an alkyl group bound through a single, terminal ether linkage; that is, an "alkoxy" group can be defined as —$OZ^1$ wherein $Z^1$ is alkyl as defined above.

The term "alkenyl" as used herein is a hydrocarbon group of from 2 to 24 carbon atoms with a structural formula containing at least one carbon-carbon double bond. Asymmetric structures such as $(Z^1Z^2)C=C(Z^3Z^4)$ are intended to include both the E- and Z-isomers. This can be presumed in structural formulae herein wherein an asymmetric alkene is present, or it can be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl or heteroaryl group can be substituted or unsubstituted. The aryl or heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. In certain specific examples cycloalkyl is a $C_{3-8}$ cycloalkyl.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (e.g., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" or "CO" is a short hand notation for C=O, which is also referred to herein as a "carbonyl."

The terms "amine" or "amino" as used herein are represented by the formula —$NZ^1Z^2$, wherein $Z^1$ and $Z^2$ can each be a substituent group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above. "Amido" is —C(O)$NZ^1Z^2$.

The term "carboxylic acid" as used herein is represented by the formula —C(O)OH. A "carboxylate" or "carboxyl" group as used herein is represented by the formula —C(O)$O^-$.

The term "ester" as used herein is represented by the formula —OC(O)$Z^1$ or —C(O)$OZ^1$, wherein $Z^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $Z^1OZ^2$, wherein $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $Z^1C(O)Z^2$, wherein $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" or "halogen" as used herein refers to fluorine, chlorine, bromine, and iodine. The corresponding term "halo", e.g., fluoro, chloro, bromo, and iodo as used herein refer to the corresponding radical or ion.

The term "hydroxyl" as used herein is represented by the formula —OH.

The term "cyano" as used herein is represented by the formula —CN. Cyanide is used to refer to the cyanide ion $CN^-$.

The term "nitro" as used herein is represented by the formula —$NO_2$.

The term "silyl" as used herein is represented by the formula —$SiZ^1Z^2Z^3$, wherein $Z^1$, $Z^2$, and $Z^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfoxo group represented by the formula —$S(O)_2Z^1$, wherein $Z^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —$S(O)_2NH$—.

The term "thiol" as used herein is represented by the formula —SH.

The term "thio" as used herein is represented by the formula —S—.

"$R^1$," "$R^2$," "$R^3$," "Re," etc., wherein n is some integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within a second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed materials, compounds, compositions, articles, and methods, examples of which are illustrated in the accompanying Examples and FIGURE.

Methods

Disclosed herein are methods for fluorinating aryl or heteroaryl substrates through in situ generation of anhydrous tetrabutylammonium fluoride (TBAF*), without the need for pre-formation. These methods are competent in a variety of solvents, and can be used effectively to fluorinate chloropyridines that are difficult to synthesize via traditional Halex methodology. Another advantage of this technology is the ability to perform fluorinations at room temperature.

In particular, disclosed herein are methods of preparing a fluorinated aryl or heteroaryl substrate that comprise combining a quaternary ammonium cyanide and an aryl or heteroaryl substrate substituted with at least one chloro, bromo, sulfonyl, or nitro group, to thereby provide a mixture and combining hexafluorobenzene and the mixture to thereby provide the fluorinated aryl or heteroaryl substrate.

Also disclosed are methods of preparing a fluorinated aryl or heteroaryl substrate that comprise combining an aryl or heteroaryl substrate substituted with at least one chloro, bromo, sulfonyl, or nitro group with hexafluorobenzene, and combining the resultant mixture with a quaternary ammonium cyanide. By these methods, TBAF* is generated in the presence of the substrate, in situ, rather than being generated beforehand and then being combined with the substrate. Thus, the disclosed methods do not involve pre-formation of TBAF*. The order of addition can be changed to suppress undesired reactivity of activated chloropyridines to form cyanopyridines.

Various quaternary ammonium cyanides can be used in the disclosed methods. These salts can be represented by the formula $(R')_4NCN$. When all four of the R' substituents are the same, the quaternary ammonium cyanide can be referred to as a "symmetrical quaternary ammonium cyanide." When one or more of the R' substituents is different from the other R' substituents, the quaternary ammonium cyanide can be referred to as an "unsymmetrical quaternary ammonium cyanide." Examples of symmetrical quaternary ammonium cyanides that can be used herein can be represented by the formula $(R')_4NCN$, wherein all R' substituents are chosen from substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted cycloalkyl, substituted or unsubstituted heterocycloalkyl, substituted or unsubstituted aryl, and substituted or unsubstituted heteroaryl. When substituted, the aforementioned R' substituents can be substituted with one or more of the following substituents: alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, and thiol. In specific examples, the symmetrical quaternary ammonium cyanide can be a tetra$C_{1-6}$ alkylammonium cyanide like tetrahexylammonium cyanide, tetrapentylammonium cyanide, tetrabutylammonium cyanide, tetrapropylammonium cyanide, tetraethylammonium cyanide, and tetramethylammonium cyanide.

Examples of unsymmetrical quaternary ammonium cyanides that can be used herein can be represented by the formula $(R')_4NCN$, wherein each R' substituent is independently chosen from substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted cycloalkyl, substituted or unsubstituted heterocycloalkyl, substituted or unsubstituted aryl, and substituted or unsubstituted heteroaryl, and wherein at least one R' is different from the other R' substituents. When substituted, the aforementioned R' substituents can be substituted with one or more of the following substituents: alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, and thiol. One specific substituent for R' is a methyl substituted with a phenyl, i.e., benzyl. In a particular example, each R' is, independent of the others, any optionally substituted $C_{1-12}$ alkyl and wherein at least one R' is different from the other R' substituents. Specific examples of unsymmetrical quaternary ammonium cyanides include tributyl(methyl)ammonium cyanide, tributyl(ethyl)ammonium cyanide, benzyltrimethylammonium cyanide, triethyl(methyl)ammonium cyanide, and trimethyl(ethyl)ammonium cyanide. Further examples of unsymmetrical quaternary ammonium cyanides can have two R' substituents that are combined to form a cyclic moiety, such as a pyrrolidine or piperidine, and the other two R' substituents can be any $C_{1-12}$ alkyl. Specific examples of these salts include dimethylpyrrolidinium cyanide and diethylpyrrolidinium cyanide. In still other examples, the quaternary ammonium salt can have phosphoranylidene substituents, an example of which includes bis(triphenylphosphoranylidene)ammonium cyanide.

The quaternary ammonium cyanides disclosed herein can be prepared by treating the corresponding quaternary ammonium halide with aqueous sodium cyanide in acetonitrile.

In the disclosed methods, the quaternary ammonium cyanide and the aryl or heteroaryl substrate can be combined in the presence of a solvent. Alternatively, the quaternary ammonium cyanide and substrate can be combined neat, without any solvent, and a solvent can then be added to the resulting mixture before it is combined with hexafluorobenzene. Alternatively or additionally, the hexafluorobenzene and the mixture of quaternary ammonium cyanide and substrate are combined in the presence of a solvent.

A variety of suitable solvents can be used. For example, the solvent can be a polar aprotic solvent. In specific examples, the solvent can be one or more of dimethylformamide, dimethylacetamide, tetrahydrofuran, sulfolane, or deuterated analogs thereof. In certain examples, the solvent can be acetonitrile or a deuterated analog thereof. In other examples, the solvent can be dimethylsulfoxide or a deuterated analog thereof. The methods disclosed herein can use any of these solvents alone or in combination with others solvents.

If used in the disclosed methods, the amount of solvent can vary depending on the particular aryl or heteroaryl substrate. In certain examples, from about 0.5 to about 5 equivalents of the solvent can be used per equivalent of the aryl or heteroaryl substrate. For example, from about 0.5 to about 4.5 equivalents, from about 0.5 to about 4 equivalents, from about 0.5 to about 3.5 equivalents, from about 0.5 to about 3 equivalents, from about 0.5 to about 2.5 equivalents, from about 0.5 to about 2 equivalents, from about 0.5 to about 1.5 equivalents, from about 0.5 to about 1 equivalent, from about 1 to about 5 equivalents, from about 1 to about 4.5 equivalents, from about 1 to about 4 equivalents, from about 1 to about 3.5 equivalents, from about 1 to about 3 equivalents, from about 1 to about 2.5 equivalents, from about 1 to about 2 equivalents, from about 1 to about 1.5 equivalents, from about 1.5 to about 5 equivalents, from about 1.5 to about 4.5 equivalents, from about 1.5 to about 4 equivalents, from about 1.5 to about 3.5 equivalents, from about 1.5 to about 3 equivalents, from about 1.5 to about 2.5 equivalents, from about 1.5 to about 2 equivalents, from about 2 to about 5 equivalents, from about 2 to about 4.5 equivalents, from about 2 to about 4 equivalents, from about 2 to about 3.5 equivalents, from about 2 to about 3 equivalents, from about 2 to about 2.5 equivalents, from about 2.5 to about 5 equivalents, from about 2.5 to about 4.5 equivalents, from about 2.5 to about 4 equivalents, from about 2.5 to about 3.5 equivalents, from about 2.5 to about 3 equivalents, from about 3 to about 5 equivalents, from about 3 to about 4.5 equivalents, from about 3 to about 4 equivalents, from about 3 to about 3.5 equivalents, from about 3.5 to about 5 equivalents, from about 3.5 to about 4.5 equivalents, from about 3.5 to about 4 equivalents, from about 4 to about 5 equivalents, from about 4 to about 4.5 equivalents, or from about 4.5 to about 5 equivalents of the solvent can be used per equivalent of the aryl or heteroaryl substrate.

The combination of the quaternary ammonium cyanide and the aryl or heteroaryl substrate can be accomplished by methods known in the art. For example, the quaternary ammonium cyanide can be added to the aryl or heteroaryl substrate. Typically, the addition can be accompanied by mixing, stirring, shaking or other form of agitation. Alternatively, the aryl or heteroaryl substrate can be added to the quaternary ammonium cyanide. Again this addition can be accompanied by mixing, stirring, shaking or other form of agitation. In still another example, the quaternary ammonium cyanide and aryl or heteroaryl substrate can be added together simultaneously. Further, the addition of these materials can be conducted at elevated temperature, e.g., from about 30° C. to about 225° C., from about 50° C. to about 200° C., from about 100° C. to about 150° C., from about 100° C. to about 225° C., from about 150° C. to about 225° C., from about 30° C. to about 100° C., from about 50° C. to about 100° C., or from about 30° C. to about 50° C. However, one particular advantage of the disclosed methods is that they can be performed at room temperature. Thus, in certain examples the quaternary ammonium cyanide and aryl or heteroaryl substrate can be combined at room temperature.

The amount of the quaternary ammonium cyanide can vary depending on the particular aryl or heteroaryl substrate. In certain examples, from about 0.5 to about 10 equivalents of the quaternary ammonium cyanide can be used per equivalent of the aryl or heteroaryl substrate. For example, from about 0.5 to about 9 equivalents, from about 0.5 to about 8 equivalents, from about 0.5 to about 7 equivalents, from about 0.5 to about 6 equivalents, from about 0.5 to about 5 equivalents, from about 0.5 to about 4 equivalents, from about 0.5 to about 3 equivalents, from about 0.5 to about 2 equivalents, from about 1 to about 10 equivalents, from about 1 to about 9 equivalents, from about 1 to about 8 equivalents, from about 1 to about 7 equivalents, from about 1 to about 6 equivalents, from about 1 to about 5 equivalents, from about 1 to about 4 equivalents, from about 1 to about 3 equivalents, from about 2 to about 10 equivalents, from about 2 to about 9 equivalents, from about 2 to about 8 equivalents, from about 2 to about 7 equivalents, from about 2 to about 6 equivalents, from about 2 to about 5 equivalents, from about 2 to about 4 equivalents, from about 2 to about 3 equivalents, from about 3 to about 10 equivalents, from about 3 to about 9 equivalents, from about 3 to about 8 equivalents, from about 3 to about 7 equivalents, from about 3 to about 6 equivalents, from about 3 to about 5 equivalents, from about 3 to about 4 equivalents, from about 4 to about 10 equivalents, from about 4 to about 9 equivalents, from about 4 to about 8 equivalents, from about 4 to about 7 equivalents, from about 4 to about 6 equivalents, from about 4 to about 5 equivalents, from about 5 to about 10 equivalents, from about 5 to about 9 equivalents, from about 5 to about 8 equivalents, from about 5 to about 7 equivalents, from about 5 to about 6 equivalents, from about 6 to about 10 equivalents, from about 6 to about 9 equivalents, from about 6 to about 8 equivalents, from about 6 to about 7 equivalents, from about 7 to about 10 equivalents, from about 7 to about 9 equivalents, from about 7 to about 8 equivalents, from about 8 to about 10 equivalents, from about 8 to about 9 equivalents, from about 9 to about 10 equivalents, or from about 0.5 to about 1 equivalents of the quaternary ammonium cyanide can be used per equivalent of the aryl or heteroaryl substrate.

The resulting mixture obtained by adding the quaternary ammonium cyanide and the aryl or heteroaryl substrate is then combined with hexafluorobenzene. This combination can be accomplished by methods known in the art. For example, the mixture can be added to hexafluorobenzene. Typically, the addition can be accompanied by mixing, stirring, shaking or other form of agitation. Alternatively, hexafluorobenzene can be added to the mixture. Again this addition can be accompanied by mixing, stirring, shaking or other form of agitation. In still another example, the mixture and hexafluorobenzene can be added together simultaneously.

Further, the addition of these materials can be conducted at elevated temperature, e.g., from about 30° C. to about 225° C., from about 50° C. to about 200° C., from about 100° C. to about 150° C., from about 100° C. to about 225° C., from about 150° C. to about 225° C., from about 30° C. to about 100° C., from about 50° C. to about 100° C., or from about 30° C. to about 50° C. However, one particular advantage of the disclosed methods is that they can be performed at room temperature. Thus, in certain examples the mixture comprising quaternary ammonium cyanide and aryl or heteroaryl substrate can be combined with hexafluorobenzene at room temperature.

The amount of hexafluorobenzene can vary depending on the particular aryl or heteroaryl substrate. In certain examples, from about 0.1 to about 5 equivalents of the hexafluorobenzene can be used per equivalent of the aryl or heteroaryl substrate. For example, from about 0.5 to about 4.5 equivalents, from about 0.5 to about 4 equivalents, from about 0.5 to about 3.5 equivalents, from about 0.5 to about 3 equivalents, from about 0.5 to about 2.5 equivalents, from about 0.5 to about 2 equivalents, from about 0.5 to about 1.5 equivalents, from about 0.5 to about 1 equivalents, from about 1 to about 5 equivalents, from about 1 to about 4.5 equivalents, from about 1 to about 4 equivalents, from about 1 to about 3.5 equivalents, from about 1 to about 3 equivalents, from about 1 to about 2.5 equivalents, from about 1 to about 2 equivalents, from about 1 to about 1.5 equivalents, from about 1.5 to about 5 equivalents, from about 1.5 to about 4.5 equivalents, from about 1.5 to about 4 equivalents, from about 1.5 to about 3.5 equivalents, from about 1.5 to about 3 equivalents, from about 1.5 to about 2.5 equivalents, from about 1.5 to about 2 equivalents, from about 2 to about 5 equivalents, from about 2 to about 4.5 equivalents, from about 2 to about 4 equivalents, from about 2 to about 3.5 equivalents, from about 2 to about 3 equivalents, from about 2 to about 2.5 equivalents, from about 2.5 to about 5 equivalents, from about 2.5 to about 4.5 equivalents, from about 2.5 to about 4 equivalents, from about 2.5 to about 3.5 equivalents, from about 2.5 to about 3 equivalents, from about 3 to about 5 equivalents, from about 3 to about 4.5 equivalents, from about 3 to about 4 equivalents, from about 3 to about 3.5 equivalents, from about 3.5 to about 5 equivalents, from about 3.5 to about 4.5 equivalents, from about 3.5 to about 4 equivalents, from about 4 to about 5 equivalents, from about 4 to about 4.5 equivalents, or from about 4.5 to about 5 equivalents of hexafluorobenzene can be used per equivalent of the aryl or heteroaryl substrate.

In specific examples of the disclosed methods, the quaternary ammonium cyanide can combined with a heteroaryl substrate having Formula IA or IB:

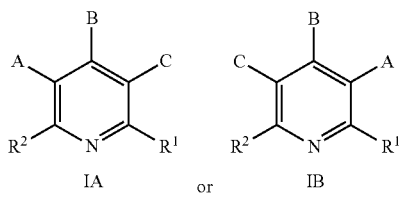

IA or IB wherein
A is Cl, Br, $SO_2R^3$, or $NO_2$;
B is H, Cl, Br, $SO_2R^3$, or $NO_2$;
C is H, Cl, Br, $SO_2R^3$, or $NO_2$;
$R^1$ is H, CN, or $CO_2R^3$, wherein each $R^3$ is, independent of any other, optionally substituted $C_1$-$C_{12}$ alkyl, $C_2$-$C_{12}$ alkenyl, $C_2$-$C_{12}$ alkynyl, heterocycloalkyl, heteroaryl, cycloalkyl, or aryl; and
$R^2$ is H, substituted or unsubstituted aryl, substituted or unsubstituted heteroaryl;
and wherein the fluorinated product has Formula IIA or IIB

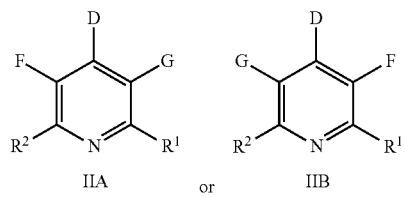

IIA or IIB wherein D is B, as defined above, or F, and G is B, as defined above, or F.

The disclosed methods can be selective in that the competing product, bisfluorinated or a para-fluorinated product, is present in an amount less than the amount of the product of Formula IIA or IIB. For example, the amount of bisfluorinated or a para-fluorinated product is less than the amount of the product of Formula IIA or IIB when D is B and G is B, as defined above.

In a further example, a fluorinated heteroaryl substrate can be prepared by mixing a quaternary ammonium cyanide, hexafluorobenzene, a solvent, and a heteroaryl substrate having Formula IA or IB:

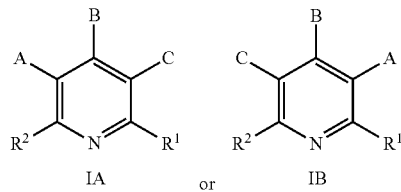

IA or IB wherein
A is Cl, Br, $SO_2R^3$, or $NO_2$;
B is H, Cl, Br, $SO_2R^3$, or $NO_2$;
C is H, Cl, Br, $SO_2R^3$, or $NO_2$;
$R^1$ is H, CN, or $CO_2R^3$, wherein each $R^3$ is, independent of any other, optionally substituted $C_1$-$C_{12}$ alkyl, $C_2$-$C_{12}$ alkenyl, $C_2$-$C_{12}$ alkynyl, heterocycloalkyl, heteroaryl, cycloalkyl, or aryl; and
$R^2$ is H, substituted or unsubstituted aryl, substituted or unsubstituted heteroaryl.

In this method the reagents are combined such that TBAF* is generated in the presence of the substrate, in situ, rather than beforehand. The quaternary ammonium cyanide that can be used in this method is as disclosed above, e.g., the quaternary ammonium cyanide can be tetrabutylammonium cyanide or tetramethylammonium cyanide. Likewise, the solvent used here can be one or more solvents disclosed above, e.g., dimethylformamide, dimethylacetamide, tetrahydrofuran, sulfolane, acetonitrile, dimethylsulfoxide, or deuterated analogs thereof. Still further, these reagents can be mixed in the same way, at the same temperature, and in the same amounts as noted above. However, an advantage of this method is that mixing can be performed at room temperature.

EXAMPLES

The following examples are set forth below to illustrate the methods, compositions, and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in degrees Celsius (° C.) or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

General Procedure for Fluorination with Pre-Formed TBAF*

Tetrabutylammonium cyanide (TBACN; 2.0-4.0 equivalents (equiv)), dried under vacuum at 40° C. for 12 hours (h), was weighed into a 4 milliliter (mL) vial (vial 1). Dimethylsulfoxide (DMSO; x mL) was added, and the mixture was stirred at room temperature until all TBACN had dissolved (<5 minutes (min)). Hexafluorobenzene ($C_6F_6$; 0.033-0.0667 equiv) was added and a rapid color change was observed. This solution was stirred at room temperature (rt) for 1 h. Chloropyridine substrate (1.0 equiv) was weighed into a separate 4 mL vial equipped with a micro stirbar and the appropriate amount of preformed TBAF* (from vial 1) was added via syringe. The vial was sealed with a Teflon-lined screwcap and the reaction vial was removed from the nitrogen ($N_2$) drybox. The reaction was placed on an IKA™ heating/stirring plate and stirred at room temperature for the given amount of time (24 h). After the reaction was complete it was diluted with dichloromethane (DCM) and an internal standard was added. Yields were determined by $^{19}F$ nuclear magnetic resonance (NMR) spectroscopy.

General Procedure for Fluorination of Heterocycles with In Situ Generated TBAF*

Chloropyridine substrate (1.0 equiv) and TBACN (2.0-4.0 equiv) were added to a 4 mL vial equipped with a micro stir bar. DMSO was added, and the mixture was stirred at room temperature until all solids had dissolved (<5 min) $C_6F_6$ (0.033-0.0667 equiv) was added and a rapid color change was observed. The vial was sealed with a Teflon-lined screwcap, and the reaction vial was removed from the $N_2$ drybox. The reaction was placed on an IKA® heating/stirring plate and stirred at room temperature for the given amount of time (24 h). After the reaction was complete it was diluted with DCM and an internal standard was added. Yields were determined by $^{19}F$ NMR spectroscopy. Procedures with aryl substrates follow analogous steps.

Pre-Formed TBAF* with DS-2

Substrate DS-2, which includes a chloropicolinate core, was used as a model substrate. Applying conditions similar to DiMagno et al. (J. Am. Chem. Soc. 2005, 127, 2050-2051; Angew. Chem. Int. Ed. 2006, 45, 2720-2725) resulted in full conversion to fluoropicloinate DS-2 within 24 h. An increase in yield was observed with increased equivalents of pre-formed TBAF* (FIG. 1).

In Situ TBAF* with DS-2

It was found that pre-formation of TBAF* is not necessary to facilitate fluorination at room temperature. Weighing the substrate and TBACN into the reaction vessel followed by DMSO and the appropriate amount of $C_6F_6$ furnishes the desired product in excellent yield (Table 1).

Scheme 1

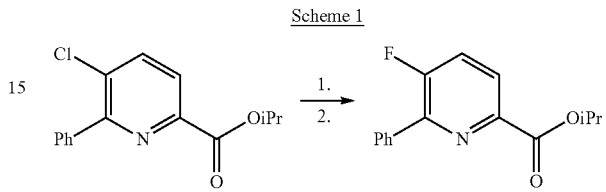

Referring to Scheme 1: (1.) TBACN (2.0-4.0 equiv); DMSO (0.72 mL); stir at rt, 5 min. (2.) $C_6F_6$ (0.33-0.66 equiv); stir at rt, 24 h.

TABLE 1

Fluorination of DS-2 with in situ generated anhydrous TBAF*

| Entry | TBAF* Equiv | Yield |
|---|---|---|
| 1 | 2.0 | >99% |
| 2 | 2.0 | >99% |
| 3 | 4.0 | >99% |
| 4 | 4.0 | >99% |

In Situ TBAF* with Different Solvents

In addition to DMSO, dimethylfomamide (DMF), dimethylacetamide (DMAc) as well as acetonitrile (MeCN) promoted the desired fluorination with high reactivity at room temperature through the in situ TBAF* methodology described above (Table 2).

Referring to Scheme 1: (1.) TBACN (2.0 equiv); solvent; stir at rt, 5 min. (2.) $C_6F_6$ (0.33-0.66 equiv); stir at rt, 24 h.

TABLE 2

Fluorination of DS-2 with in situ generated anhydrous TBAF*

| Entry | Solvent | Yield |
|---|---|---|
| 1 | 2.0 | >99% |
| 2 | 2.0 | >99% |
| 3 | 4.0 | >99% |
| 4 | 4.0 | >99% |

In Situ TBAF* with Different Substrates

In addition to the model substrate DS-2, other chloropicolinates, as well as simple chloropyridines, underwent fluorination with the disclosed methods. 5-Chloropicolinates went to full conversion as demonstrated in Scheme 2 (top row). 5-Fluoropicolinic acid, however, was only formed in small quantities presumably due to deprotonation by fluoride thereby inactivating the substrate to nucleophilic aromatic substitution. Simpler chloropyridines were less effective as substrates for this method in accordance to the reactivity observed by DiMagno et al. 4,5-Dichloro-6-arylpicolinates (Scheme 2, bottom row) demonstrated fluorination first at the more activated 4-position followed by fluorination of the less activated 5-position, although the total yield was diminished due to the production of the undesired bis-cyanopicolinate product.

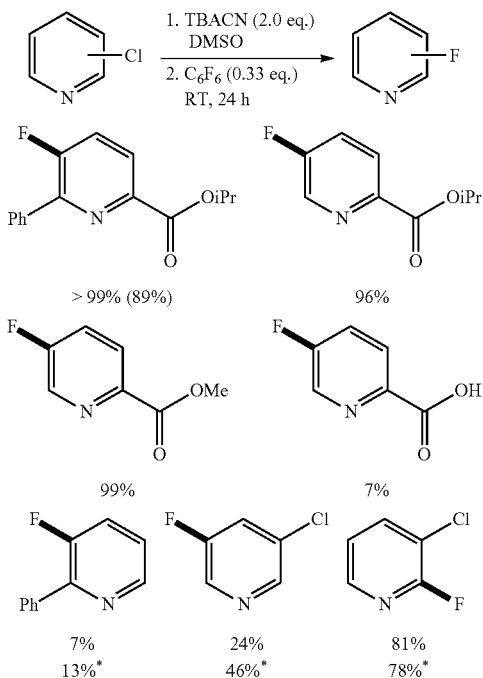

Scheme 2

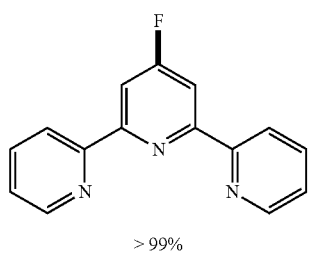

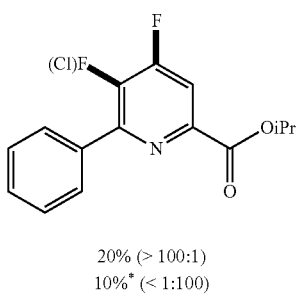

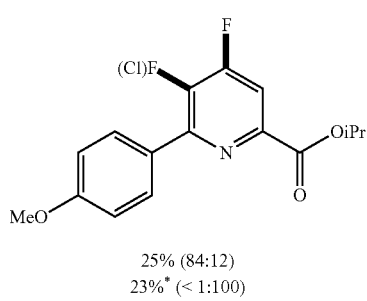

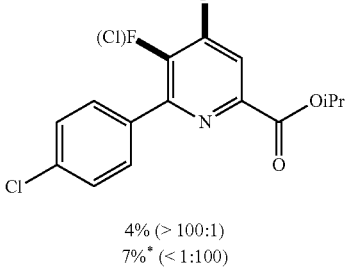

4% (>100:1)
7%* (<1:100)

Yield given as 19F NMR yield with trifluorotoluene as internal standard.* = 4.0/0.667 eq. TBACN/ 0 = mono fluorinated: bisflorinated pdt.

To avoid formation of the undesired bis-cyanopicolinate, the order of addition was reversed. Tetrabutylammonium cyanide was dissolved in DMSO (or MeCN) followed by the addition of $C_6F_6$ (Scheme 3). The 4,5-dichloro-6-arylpicolinate substrate was then added and the reaction was stirred at room temperature for 24 h. This method provided 95% total yield for R=H, 90% for R=4-OMe, and 75% for R=Cl, an improvement over the previous method still without the need for pre-formation (Table 3).

Scheme 3

TBACN (2.0 equiv) 
1. DMSO
2. $C_6F_6$ (0.33 equiv)
3. Substrate (1 equiv)
rt, 24 h

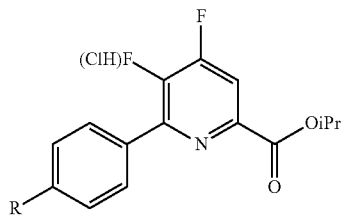

TABLE 3

Fluorination of 4,5-dichloro-6-arylpicolinates with in situ TBAF*

| Entry | R | Solvent | Total Yield | Mono:Bis |
|---|---|---|---|---|
| 1 | H | DMSO | 90% | 44:55 |
| 2 | H | MeCN | 68% | 59:41 |
| 3 | OMe | DMSO | 95% | 36:64 |
| 4 | OMe | MeCN | 75% | 44:55 |
| 5 | Cl | DMSO | 73% | 23:77 |

The materials and methods of the appended claims are not limited in scope by the specific materials and methods described herein, which are intended as illustrations of a few aspects of the claims and any materials and methods that are functionally equivalent are within the scope of this disclosure. Various modifications of the materials and methods in addition to those shown and described herein are intended to fall within the scope of the appended claims. Further, while only certain representative materials, methods, and aspects of these materials and methods are specifically described, other materials and methods and combinations of various features of the materials and methods are intended to fall within the scope of the appended claims, even if not specifically recited. Thus a combination of steps, elements, components, or constituents can be explicitly mentioned herein; however, all other combinations of steps, elements, components, and constituents are included, even though not explicitly stated.

Contrasting Summary Example

For Table 4, the yield for in situ generated TBAF*, as shown in the reaction scheme, is shown in the first entry. The first percent yield noted is from fluorine NMR and the percent yield in parentheses is isolated yield. These results are shown in Table 4 with fluorinations using various other conditions, as noted. All of the reactions were done in DMSO.

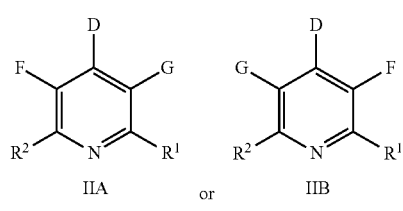

| Conditions | $^{19}$F NMR Yield |
|---|---|
| TBACN/C$_6$F$_6$ (rt/2.0 equiv) | 80% (65%) |
| CsF (130° C./2.0 equiv) | 35% |
| KF (130° C./2.0 equiv) | 0% |
| KF/PTC (130° C./2.0 equiv)* | 7% |

Unsymmetrical Quaternary Ammonium Salts*

An unsymmetrical quaternary ammonium cyanide, namely tetrabutyl(methyl)-ammonium cyanide was prepared from the corresponding ammonium chlorine and sodium cyanide as shown in Scheme 4. The in situ generated fluoride salt by treatment with hexafluorobenzene in DMSO at room temperature lead to the fluorinated substrate in Scheme 4 in 80% yield.

Scheme 4

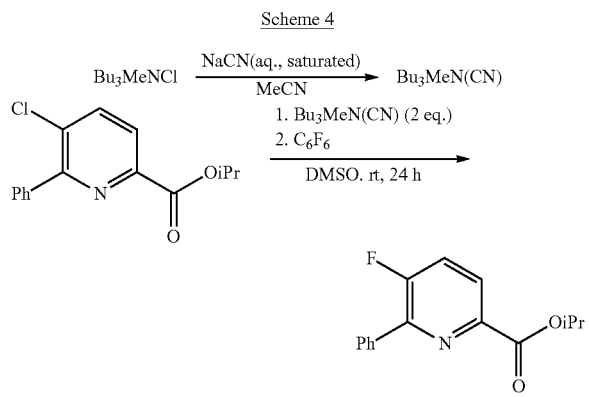

What is claimed is:
1. A method of preparing a fluorinated heteroaryl substrate, comprising:
   (a) combining a quaternary ammonium cyanide and a heteroaryl substrate having Formula IA or IB:

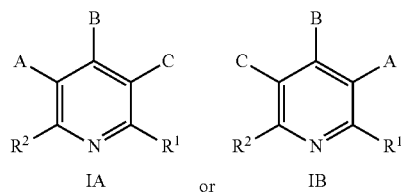

wherein
A is Cl, Br, SO$_2$R$^3$, or NO$_2$;
B is H, Cl, Br, SO$_2$R$^3$, or NO$_2$;
C is H, Cl, Br, SO$_2$R$^3$, or NO$_2$;
R$^1$ is CO$_2$R$^3$, wherein R$^3$ is optionally substituted C$_1$-C$_{12}$ alkyl, C$_2$-C$_{12}$ alkenyl, C$_2$-C$_{12}$ alkynyl, heterocycloalkyl, heteroaryl, cycloalkyl, or aryl;
R$^2$ is substituted or unsubstituted aryl, or substituted or unsubstituted heteroaryl, thereby providing a mixture; and
(b) combining hexafluorobenzene and the mixture to thereby provide the fluorinated heteroaryl substrate having Formula IIA or IIB

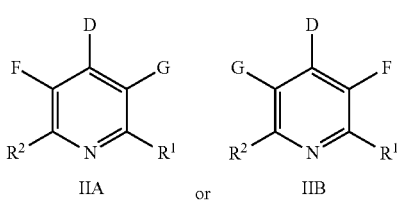

wherein D is B or F, and G is B or F.
2. The method of claim 1, wherein the quaternary ammonium cyanide is tetrabutylammonium cyanide.
3. The method of claim 1, wherein the quaternary ammonium cyanide is tetramethylammonium cyanide.
4. The method of claim 1, wherein the quaternary ammonium cyanide is chosen from tetrahexylammonium cyanide, tetrapentylammonium cyanide, tetrapropylammonium cyanide, tetraethylammonium cyanide, tributyl(methyl)ammonium cyanide, tributyl(ethyl)ammonium cyanide, benzyltrimethylammonium cyanide, bis(triphenylphosphoranylidene)ammonium cyanide, triethyl(methyl)ammonium cyanide, and trimethyl(ethyl)ammonium cyanide, dimethylpyrrolidinium cyanide, and diethylpyrrolidinium cyanide.
5. The method of claim 1, wherein the quaternary ammonium cyanide and the heteroaryl substrate are combined in the presence of a solvent.
6. The method of claim 1, wherein the hexafluorobenzene and the mixture are combined in the presence of a solvent.
7. The method of claim 1, further comprising adding a solvent to the mixture before combining the mixture with hexafluorobenzene.
8. The method of claim 5, wherein the solvent is a polar aprotic solvent.
9. The method of claim 5, wherein the solvent is one or more of dimethylformamide, dimethylacetamide, tetrahydrofuran, sulfolane, or deuterated analogs thereof.
10. The method of claim 5, wherein the solvent is acetonitrile or a deuterated analog thereof.
11. The method of claim 5, wherein the solvent is dimethylsulfoxide or a deuterated analog thereof.

12. The method of claim 5, wherein from 0.5 to 5 equivalents of the solvent is used per equivalent of the heteroaryl substrate.

13. The method of claim 1, wherein the quaternary ammonium cyanide and the heteroaryl substrate are combined at room temperature.

14. The method of claim 1, wherein the hexafluorobenzene and the mixture are combined at room temperature.

15. The method of claim 1, wherein from 0.5 to 10 equivalents of the quaternary ammonium cyanide is used per equivalent of the heteroaryl substrate.

16. The method of claim 1, wherein from 0.1 to 5 equivalents of hexafluorobenzene is used per equivalent of the heteroaryl substrate.

17. The method of claim 1, wherein a difluorinated or a para-fluorinated product is present in an amount less than the amount of Formula IIA or IIB.

* * * * *